United States Patent
Danchin et al.

(10) Patent No.: US 9,610,236 B2
(45) Date of Patent: Apr. 4, 2017

(54) COSMETIC USE OF QUEUINE

(71) Applicant: AMABIOTICS, Paris (FR)

(72) Inventors: Antoine Danchin, Paris (FR); Agnieszka Sekowska, Paris (FR)

(73) Assignee: AMABIOTICS, Paris (FR)

( * ) Notice: Subject to any disclaimer, the term of this patent is extended or adjusted under 35 U.S.C. 154(b) by 0 days.

(21) Appl. No.: 14/769,188

(22) PCT Filed: Feb. 18, 2014

(86) PCT No.: PCT/EP2014/053143
§ 371 (c)(1),
(2) Date: Aug. 20, 2015

(87) PCT Pub. No.: WO2014/128126
PCT Pub. Date: Aug. 28, 2014

(65) Prior Publication Data
US 2016/0008252 A1 Jan. 14, 2016

(30) Foreign Application Priority Data

Feb. 21, 2013 (FR) ..................... 13 51486

(51) Int. Cl.
| | |
|---|---|
| *A61Q 19/08* | (2006.01) |
| *A61K 8/49* | (2006.01) |
| *A61K 8/60* | (2006.01) |
| *A61Q 1/06* | (2006.01) |
| *A61Q 1/10* | (2006.01) |
| *A61Q 5/02* | (2006.01) |
| *A61Q 5/12* | (2006.01) |

(52) U.S. Cl.
CPC ............ *A61K 8/4953* (2013.01); *A61K 8/602* (2013.01); *A61Q 1/06* (2013.01); *A61Q 1/10* (2013.01); *A61Q 5/02* (2013.01); *A61Q 5/12* (2013.01); *A61Q 19/08* (2013.01)

(58) Field of Classification Search
None
See application file for complete search history.

(56) References Cited

U.S. PATENT DOCUMENTS

| | | |
|---|---|---|
| 5,312,900 A | 5/1994 | Armstrong |
| 6,020,139 A * | 2/2000 | Schwartz ............ A61K 31/198 435/192 |
| 2004/0091509 A1 | 5/2004 | Anderson et al. |

OTHER PUBLICATIONS

Fusco, D., et al., "Effects of antioxidant supplementation on the aging process" *Clinical Interventions in Aging*, Jan. 1, 2007, vol. 2, No. 3, pp. 377-387.
Pathak, C., et al., "Modulation in the activity of lactate dehydrogenase and level of c-Myc and c-Fos by modified base queuine in cancer" *Cancer Biology & Therapy*, Jan. 1, 2008, vol. 7, No. 1, pp. 85-91.
Pathak, C., et al., "Queuine promotes antioxidant defence system by activating cellular antioxidant enzyme activities in cancer" *Bioscience Reports*, Apr. 1, 2008, vol. 28, No. 2, pp. 73-81.
Written Opinion in International Application No. PCT/EP2014/053143, Oct. 31, 2014, pp. 1-7.

* cited by examiner

*Primary Examiner* — Ali Soroush
(74) *Attorney, Agent, or Firm* — Saliwanchik, Lloyd & Eisenschenk

(57) ABSTRACT

The present invention relates to the cosmetic use of queuine, in particular to combat aging of the skin. It also relates to a cosmetic composition comprising queuine as an active ingredient.

7 Claims, 3 Drawing Sheets

COSMETIC USE OF QUEUINE

CROSS-REFERENCE TO RELATED APPLICATION

This application is the U.S. national stage application of International Patent Application No. PCT/EP2014/053143, filed Feb. 18, 2014.

FIELD OF THE INVENTION

The present invention pertains to the field of cosmetics, in particular products to prevent or combat aging of the skin and skin appendages.

BACKGROUND OF THE INVENTION

As protective tissue and exchange boundary, the skin is rapidly renewed throughout a lifetime. Passing time inevitably results in aging of the skin. Premature aging may even occur as a consequence of multiple environmental attacks. As an interface with the outside environment, skin is constantly subjected to damage resulting from all kinds of physicochemical attacks: temperature change, humidity, light, pollution, etc. The skin cells age, become senescent and die after about 80 divisions. Throughout this process the skin loses its thickness and elasticity, causing the onset of wrinkles, and it also loses its protective role in particular against daytime UV radiation. It can also have irregular pigmentation (age spots).

The molecular causes of skin aging involve all the compartments of the skin. As in other tissues, some proteins induced by stress play a central protective role, in particular the chaperone proteins, which allow suitable folding of proteins and correct the defects of this folding, and proteases, which degrade chemically-deteriorated or misfolded proteins The process of translation and folding gradually becomes less efficient as cells age, thereby resulting in the occurrence of and increased sensitivity to accidental oxidising modifications and glycations. Reactive oxygen species alter the amino acids (in particular cysteine, histidine, methionine, tyrosine and tryptophan) and protein backbones. They also cause upstream deterioration of processes which lead to the synthesis of new proteins.

The accumulation of protein aggregates during the aging process progressively submerges the machinery controlling the quality of cell proteins. This aging of the skin entails degradation of the extracellular matrix both at the epidermal and dermal layers, leaving visible signs of aging on the surface of the skin and modifying the physical properties thereof.

The overall consequence is also a deterioration of normal enzymatic activity and an aggregation of whole proteins, leading to visible signs such as irregular dryness, irregular pigmentation, deep wrinkles, waxy and/or parchment complexion, sagging of the skin, etc.

Three processes enable the cells to overcome aging: neo-synthesis, repair and degradation followed by re-synthesis. Over the long term the last two processes are essential since they allow cell rejuvenation.

There is therefore a need and strong demand for novel cosmetic care products to combat aging of the skin.

DESCRIPTION OF THE INVENTION

The inventors have surprisingly discovered that an exogenous supply of queuine remedies the deleterious effects of stress inevitably undergone by the skin, thereby delaying the onset of the signs of aging. Queuine makes a major contribution to cell maintenance. Queuine has a protective effect against multiple repeated stresses. More particularly the present invention has focused on the need to optimise the process of protein re-synthesis by providing the cells with queuine. Indeed, this molecule is necessary for the optimal performing of protein synthesis and the body is unable to produce this molecule. It has been found in the setting of the present invention that an exogenous supply of queuine surprisingly contributes to the resistance of skin cells. The present invention therefore relates to a cosmetic composition comprising queuine, or a precursor or derivative thereof, as active ingredient. More particularly the subject of the invention is a cosmetic composition for topical application.

The present invention also relates to the use of queuine or a precursor or derivative thereof as an active ingredient in a cosmetic composition, and most particularly a cosmetic composition for topical application.

A further subject of the invention is the cosmetic use of queuine or a precursor or derivative thereof as an active ingredient to reduce or prevent signs of aging of the skin and/or skin appendages. "Skin appendages" preferably means the hair and nails.

The use or composition of the invention is most particularly intended to reduce or prevent wrinkles and lines, sagging of the skin, lack of elasticity and/or skin tonicity, thinning of the skin, waxy and/or parchment-like complexion, and/or irregularities in skin texture and pigmentation irregularities such as age spots.

The invention also concerns a method to prepare a cosmetic composition comprising the adding of queuine or a precursor or derivative thereof to some or all components of the cosmetic composition and the recovery of the cosmetic composition obtained.

The present invention also concerns a cosmetic treatment process to prevent and/or treat signs of aging of the skin and/or skin appendages, comprising the application to the skin and/or skin appendages of a cosmetic composition according to the invention.

In one particular embodiment the queuine or the precursor or derivative thereof is selected from the group formed by queuine, queuosine, epoxyqueuosine and epoxyqueuine. Amongst these derivatives are the glycosylated derivatives of queuine and queuosine, such as mannosylqueuine, galactosylqueuine, and aminoacylated derivatives such as glutamylqueuine. The queuine or a precursor or derivative thereof may be in purified form or in the form of a bacterial extract or plant extract or sap, said extract or said sap being rich in or enriched with queuine or a precursor or derivative thereof. In one particularly preferred embodiment the cosmetic composition comprises queuine.

Preferably the queuine or the precursor or derivative thereof is contained in the cosmetic composition in an amount of 0.1 µg to 100 µg per ml or g of cosmetic composition, preferably 0.5 to 10 µg per ml or g of cosmetic composition, and further preferably 1 to 5 µg per ml or g of cosmetic composition. For slow release derivatives the concentrations are calculated so that the rate of release at all times meets the aforementioned conditions conforming to the physicochemical release process. Optionally the cosmetic composition may comprise queuine or the precursor or derivative thereof in an amount of at least 0.1 µg to 100 µg per ml or g of cosmetic composition, more preferably at least 0.5 to 10 µg per ml or g of cosmetic composition and further preferably at least 1 to 5 µg per ml or g of cosmetic composition.

The cosmetic composition may be in the form of a serum, lotion, cream, milk, water or oil gel, hydrogel, microemulsion, nanoemulsion, mask, stick, patch, oil, unguent, wax, foam, toner, care solution, balm, foundation, spray, eye shadow, slimming cream, lipstick, paste, ointment, shampoo or conditioner, or in any suitable homogeneous or heterogeneous form allowing use of queuine and derivatives thereof.

Queuine and Precursors and Derivatives Thereof

Queuine is also known under the following chemical name: 2-amino-5-((((1s,4s,5r)-4,5-dihydroxy-2-cyclopenten-1-yl)amino)methyl)-1,7-dihydro-4h-pyrrolo(2,3-d)pyrimidin-4-one. (CAS Number: 72496-59-4)

Epoxyqueuine is also known under the following chemical name: 7-(5-[(3,4-epoxy-2,5-dihydroxycyclopent-1-yl)amino]methyl)-7-deazaguanine 2-amino-5-({[(1R,2R,3R,4R,5S)-3,4-dihydroxy-6-oxabicyclo[3.1.0]hex-2-yl]amino}methyl)-3,7-dihydro-4H-pyrrolo[2,3-d]pyrimidin-4-one. (CID Number: 56927905)

Queuosine is also known under the following chemical name: 2-amino-5-[[[(1S,4S,5R)-4,5-dihydroxy-1-cyclopent-2-enyl]amino]methyl]-7-[(2R,3R,4S,5R)-3,4-dihydroxy-5-(hydroxymethyl)-2-tetrahydrofuranyl]-1H-pyrrolo[3,2-e]pyrimidin-4-one. (CAS Number: 57072-36-3)

Epoxyqueuosine is also known under the following chemical name: 7-(5-[(3,4-epoxy-2,5-dihydroxycyclopent-1-yl)amino]methyl)-7-deazaguanosine2-amino-5-({[(1R,2R,3R,4R,5S)-3,4-dihydroxy-6-oxabicyclo[3.1.0]hex-2-yl]amino}methyl)-7-(beta-D-ribofuranosyl)-3,7-dihydro-4H-pyrrolo[2,3-d]pyrimidin-4-one. (CID Number: 56927875)

Within the context of the present application, a derivative of queuine refers to any molecule or macromolecule comprising queuine in a form adapted for use on the skin or skin appendages. In particular, queuine may be in free form or it may be part of a covalent or ionic complex. For example, it can be complexed with a ribose to form queuosine, a galactosyl queuosine, a mannosyl queuosine or a glutamyl queuosine. It can also be considered in the form of tRNA-queuosine or an oligonucleotide comprising queuosine. Among these derivatives are the glycosylated derivatives of queuine and queuosine, such as mannosylqueuine, galactosylqueuine, and aminoacylated derivatives such as glutamylqueuine.

Within the context of the present application, a precursor of queuine refers for example to its intermediate precursor, epoxyqueuine, whether in free form or in the form of a covalent complex with molecules or macromolecules.

A derivative of queuine may also be a chemically modified queuine which can be easily metabolised to queuine by enzymes such as those present on the surface of the skin. Other derivatives of queuine are derivatives which release queuine when applied to the surface of the skin or skin appendages and subjected to physicochemical treatment (e.g., natural or artificial UV light).

Preferably queuine and the precursors and derivatives thereof can be prepared by chemical synthesis. The chemical synthesis of queuine is known. In particular, two main synthesis pathways have been described (Barnett and Grubb, 2000, Tetrahedron 56, 9221-9225; Brooks et al., 2010, Tetrahedron Letters 51, 4163-4165) and can be implemented by the person skilled in the art.

Alternatively queuine and the precursors and derivatives thereof can be obtained using bacteria which synthesise such molecules.

Thus, queuine can be obtained by purifying extracts of microorganisms, bacterial microorganisms in particular.

Alternatively queuine and the precursors and derivatives thereof are in the form of bacterial extracts, possibly enriched with queuine or the precursors or derivatives thereof.

Preferably, the bacterial extract is an extract of bacteria selected from among edible Firmicutes bacteria, preferably strains of *Bacillus subtilis* or its neighbour *Bacillus amyloliquifaciens*, but also non-pathogenic *Bacillus cereus*, queuine-producing *Streptococcus thermophilus*, non-pathogenic *Staphylococcus epidermidis* and in general non-pathogenic Firmicutes, preferably used in foods. Among the Gram-negative bacteria, the gamma-Proteobacteria probiotics such as *E. coli* Nissle 1917, or proteobacteria used in foods such as *Zymononas mobilis*, are preferred. Non-toxicogenic cyanobacteria are also preferred sources of queuine, in particular the edible species *Arthrospira* (Spirulina).

In another embodiment, queuine and the precursors and derivatives thereof can be obtained from plants which have extracted these molecules from their environment, after verification of their queuine content or derivative content. In particular, plants having nodules with alpha-proteobacteria, particularly the species *Rhizobium, Mesorhizobium* and *Sinorhizobium* are an excellent source of queuine. In addition plant sap is also a source of queuine of interest if plant growth has been ensured in a microbial environment rich in bacteria adapted to the rhizosphere or if they have been colonised by epiphyte and endophyte microorganisms which synthesize queuine, in particular the Bacteroidetes, Firmicutes and Proteobacteria families (including but not limited to *Pseudomonas fluorescens* or *Serratia marcescens*). The extracts (leaves, roots, fruit, bark) of the plants used can be organisms routinely used in foods, in cosmetics or in traditional medicine, for example plants as varied as *Acalypha indica, Acanthus ebracteatus, Aloe vera, Avena sativa, Cocos nucifera, Coffea arabica, Colocasia esculenta, Curcuma longa, Hippophae rhamnoides, Jasminum sambac, Juglans mandshurica, Matricaria recutita, Mesembryanthemum crystallinum, Opuntia ficus indica, Oryza sativa, Pittocaulon praecox, Plagiochila beddomei, Populus balsamifera, Psidium guajava, Scutellaria baicalensis, Vaccinium* spp., and *Vitis vinifera*, in relation to their queuine content that is to be evaluated. Plants traditionally used for their positive effect for breeding purposes, often from the Fabaceae, Solanaceae or Asteraceae families but comprising a very large number of plants recognised as having an effect on skin quality and resistance, can be selected. Soil-less culture without microbe or queuine supply is only used provided an exogenous supply of the molecule is added. However rare or protected plants, such as *Leontopodium alpinum*, grown in the laboratory can be selected if they are grown in the presence of queuine-producing microorganisms and after evaluation of their ability to capture and concentrate the molecule.

The content of queuine, of its precursors and derivatives, and of bacterial or plant extracts is preferably guaranteed. On this account, due to degradation of microbial flora associated with plant extracts obtained from intensive culture, these extracts are preferably only used in the preparations with an exogenous supply of queuine. In general, the bacterial or plant extracts can be enriched with queuine and the precursors and derivatives thereof.

Cosmetic Composition

According to the invention, queuine, a precursor and/or derivative of queuine can be used as an active ingredient in a cosmetic composition intended to prevent or treat chronological and/or photo-induced signs of skin aging, in particular signs of early aging affecting persons aged 25-30 years and most often translating as the onset of lines and/or a dull and/or heterogeneous appearance of the complexion.

The composition of the invention comprises a physiologically acceptable medium, i.e., compatible with the skin and/or skin appendages. It is preferably a cosmetically acceptable medium, i.e., of pleasant colour, smell and consistency and which does not generate discomfort such as prickling, redness or other discomfort likely to turn consumers away from use thereof.

According to the invention, the cosmetic composition is a care or make-up product, for example in the form of a serum, lotion, cream, milk, water or oil gel, hydrogel, mask, stick, patch, oil, unguent, wax, foam, toner, care solution, balm, foundation, spray, eye shadow, lipstick, paste, ointment, shampoo or conditioner.

The cosmetic composition can also be used as a slimming composition comprising a slimming agent in addition to queuine and/or a precursor and/or derivative of queuine.

Since the composition is intended for topical administration to the skin and/or skin appendages, it may be in the form of any preparation conventionally used for topical application. In particular, it may advantageously be in the form of aqueous solutions, hydroalcoholic solutions, oil-in-water emulsions (O/W), water-in-oil emulsions (W/O), multiple emulsions (triple: W/O/W or O/W/O), or micro- or nano-emulsions.

When the composition is in aqueous form, in particular in a dispersion, emulsion or aqueous solution, it may comprise an aqueous phase possibly containing water, flower water and/or mineral water.

Such compositions may also contain usual, suitable pharmaceutically or cosmetically acceptable carriers or diluents, in particular diluting agents, dispersing agents, gelling agents, solid emollients, gums, resins, solvents, fillers such as modified and polymerised starches, titanium dioxide or metal stearate, preserving agents, essential oils, pearling agents, colouring agents, odour absorbers, pH regulators or neutralising agents, thickening agents, absorption-promoting agents and in particular ethanol and/or phospholipids, flavouring or perfuming agents, mineral pigments such as iron oxides, oil agents such as oils or fat of vegetable origin, fats of animal origin, synthetic oils, silicone oils (cyclomethicone), fluorine-containing oils, fatty alcohol esters (cetyl alcohol), waxes, modified clays, bentones, fatty acid metal salts, hydrophobized silica, polyethylenes, mica and/or other substances used in cosmetics.

The cosmetic composition of the invention may further comprise other active molecules such as vitamins, sunscreens and filters, anti-age active substances, anti-wrinkle agents (in particular peptides), anti-oxidants, lightening agents, self-tanning ingredients, tanning accelerators, lifting ingredients, slimming agents, firming ingredients, hydrating ingredients, peeling ingredients, sebum regulating agents, mattifying agents, etc. Preferably the cosmetic composition may comprise anti-age active substances, anti-wrinkle and/or anti-oxidant agents, a lifting ingredient, a firming ingredient and/or a hydrating ingredient. In general persons skilled in the art are able to select and adapt the quantities of additional active molecules so that the properties of the composition of the invention are not deteriorated through the addition thereof.

In one preferred embodiment, the queuine or precursor or derivative thereof is contained in the cosmetic composition with co-factors or vitamins such as vitamin C or tocopherol.

The invention will be better understood on reading the following experiments and examples and on examining the accompanying Figures. These are given for illustration purposes and in no way limit the invention.

EXPERIMENTS

Figure 1:
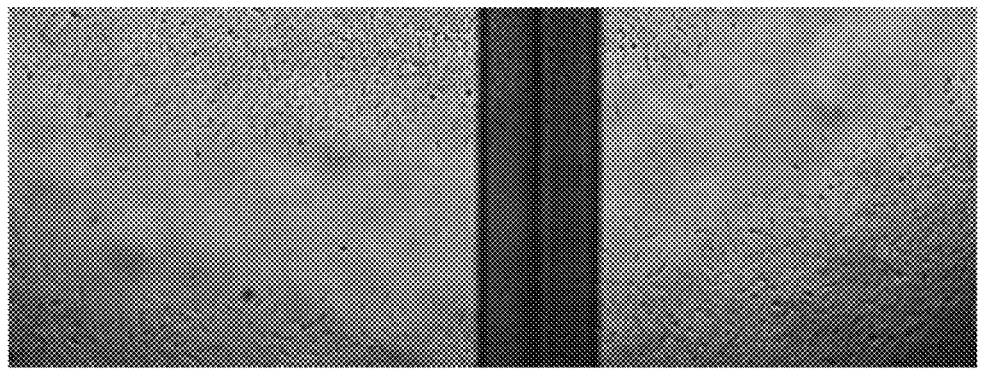
FIGS. 1, 2 and 3 show cell migration in a fibroblast culture incubated in DMEM, 2.5% FCS at 0 hours (FIG. 1) and 24 hours (FIG. 2), or in DMEM, 10% FCS at 24 hours (FIG. 3).

In these experiments, the effects of queuine (cytotoxicity, proliferation, cell migration) were evaluated in normal adult human dermal fibroblasts.

Material and Methods

Foetal calf serum (FCS), Dutscher, P30-8100M (batch P130903) was selected for use with queuine, which does not contaminate the medium.

Methanol was used here as a carrier for the active molecule.

The stock solution of queuine was prepared with 15 mg/ml methanol and the dilutions were obtained in DMEM (Dulbecco's Modified Essential Medium) in the presence of variable concentrations of foetal calf serum (FCS) (DMEM+ 2.5% FCS+antibiotics (penicillin/streptomycin)+glutamine): depleted medium with 2.5% FCS for the viability, proliferation and cell migration experiments.

Dilution Ranges

The dilution range prepared for the toxicity/viability assay was the following:

TABLE 1

| Dilution range for the toxicity/viability assay | |
|---|---|
| Queuine concentrations (µg/ml) | Final methanol percentage (%) |
| 100 | 0.6 |
| 10 | 0.06 |
| 1 | 0.006 |
| 0.1 | 0.0006 |

This first assay allowed fine-tuning of the applied concentration range.

The dilution range for the assay of cell proliferation kinetics was as follows:

TABLE 2

| Dilution range for assay of cell proliferation kinetics | |
|---|---|
| Queuine concentrations (µg/ml) | Final methanol percentage (%) |
| 30 | 0.18 |
| 10 | 0.06 |
| 3 | 0.018 |
| 1 | 0.006 |
| 0.3 | 0.0018 |

The dilution range prepared for evaluating migration was identical to the range for evaluating kinetics with the exclusion of the 0.3 µg/ml concentration.

Products Used:

TABLE 3

List of products used

| Product | Supplier | Reference |
|---|---|---|
| DMEM w/o L-glutamine | Dutscher | L0101-500 |
| PBS 1X, w/o Ca Mg | PAA | H15-002 |
| Penicillin/streptomycin | PAA | P11-010 |
| L-Glutamine | PAA | M11-004 |
| Trypsine-EDTA 10X | PAA | L11-003 |
| FCS | Dutscher | P30-8100M |
| BrdU | Roche | 11647229001 |
| MTT | Calbiochem | 475989 |
| Collagen | Nutacon | NBC__100A |
| HDFa | TebuBio | 106-05a |

Experimental Protocols
1. Cell Line

Cell type: HDFa, adult human dermal fibroblasts, female aged 39 years, used between passage 4 and passage 6.

For all the conducted experiments, the three following FCS controls were systematically added:
  serum-free DMEM;
  serum-depleted medium (DMEM supplemented with 2.5% FCS); and
  complete medium (DMEM supplemented with 10% FCS).

2. Evaluation of Cytotoxicity and Cell Proliferation

The adult HDFs used were seeded to a proportion of $5 \times 10^3$ cells/well in 96-well plates (passage 4) in 200 µl culture medium without FCS (supplemented DMEM+0% FCS). 24 h after seeding, the culture medium was changed and the different dilutions of the product or its carrier (methanol) were added at 200 µl per well, with 3 wells per culture condition.

3 controls were also evaluated (3 wells/control):
  serum-free DMEM;
  serum-depleted medium (supplemented DMEM+2.5% FCS); and
  complete medium (supplemented DMEM+10% FCS).

3. Cell Migration

The adult HDFs used were seeded in the presence of previously sterilised culture inserts which allowed the creation of calibrated acellular regions. 100,000 HDFa in 600 µl and 30,000 cells in 150 µl were respectively added outside and inside the inserts, in DMEM+2.5% FCS. After an incubation time of 5 h at 37° C., the inserts were removed and the wells washed twice with PBS 1× to eliminate every cell which had not adhered. The queuine molecule was then added at 30, 10, 3 or 1 µg/ml in DMEM 2.5% FCS, and an equivalent range of methanol was also carried out, two wells per condition. The wells were photographed at t=0 h and the plates then incubated for 24 h. The cells were fixed with paraformaldehyde before taking photos at 24 h.

Measurements and Analysis of Results
1. Quantitation of Cytotoxicity: MTT Assay

Cell proliferation was evaluated using a colorimetric assay (MTT assay) after culture times of 1, 2 and 3 days. This assay is based on reduction of the yellow tetrazolium salt (MTT) [3-(4,5-dimethylthiazol bromide] to a blue-purple formazan product by the mitochondrial NADPH reductases of the cells, provided they are living. The crystals were then dissolved in 100% ethanol—DMSO mixture (v/v). Colouring of the supernatant, proportional to the number of living cells, was measured by optical density (OD) read-out on a spectrophotometer at a wavelength of 570 nm. The assay was conducted at D1, D2 and D3 (D0 corresponding to the time of addition of the solutions to be assayed).

The mean OD values of the triplicates are given on a graph for each kinetic time. Standard deviations are indicated.

2. Quantitation of Cell Proliferation: BrdU Assay

Cell proliferation was evaluated using an assay of ELISA type (BrdU assay, Bromodeoxyuridine) after 1, 2 and 3 days of culture.

BrdU is a synthetic nucleoside and an analogue of thymidine, which can be recognised by an anti-BrdU antibody. It is incorporated during DNA replication of the proliferating cells. The anti-BrdU antibody is coupled to an enzyme which, in the presence of its substrate, will degrade the latter. Detection of BrdU is therefore carried out by colorimetric enzymatic assay.

Degradation of the enzyme substrate will stain the supernatant proportional to the amount of incorporated BrdU. Measurement is then performed by read-out of optical density (OD) using a spectrophotometer at a wavelength of 450 nm. The assay was conducted at D1, D2 and D3 (D0 corresponding to the time of addition of the solutions to be assayed).

The mean OD values, standard deviations and dose-response figures are detailed below for each kinetic time.

3. Quantitation of Cell Migration: Comparison of Migration Images Relative to Controls The images were analysed using ImageJ software, to improve the contrast thereof. All fields were examined and the two most representative of each condition were chosen for each time indication. Analysis was performed by comparison with the control.

Results
Cell Viability

TABLE 4

Cell viability after 24 h contact time

| | Queuine 0.1 µg/ml | Queuine 1 µg/ml | Queuine 10 µg/ml | Queuine 100 µg/ml | Methanol 0.0006% | Methanol 0.006% | Methanol 0.06% | Methanol 0.6% |
|---|---|---|---|---|---|---|---|---|
| OD mean values | 0.228 | 0.250 | 0.246 | 0.233 | 0.242 | 0.250 | 0.259 | 0.248 |
| | | | | | 10% FCS 0.273 | 5% FCS 0.303 | 0% FCS 0.187 | No cells 0.095 |
| Mean -blank | 0.133 | 0.155 | 0.151 | 0.138 | 0.146 | 0.154 | 0.164 | 0.153 |
| | | | | | 10% FCS 0.177 | 5% FCS 0.207 | 0% FCS 0.091 | No cells 0.000 |
| St. Devtn. | 0.007 | 0.006 | 0.011 | 0.004 | 0.014 | 0.023 | 0.019 | 0.010 |
| | | | | | 10% FCS 0.019 | 5% FCS 0.017 | 0% FCS 0.014 | No cells 0.005 |

TABLE 5

Cell viability after 48 h contact time

| | Queuine 0.1 µg/ml | Queuine 1 µg/ml | Queuine 10 µg/ml | Queuine 100 µg/ml | Methanol 0.0006% | Methanol 0.006% | Methanol 0.06% | Methanol 0.6% |
|---|---|---|---|---|---|---|---|---|
| Mean OD values | 0.304 | 0.331 | 0.328 | 0.273 | 0.329 | 0.315 | 0.324 | 0.345 |
| | | | | | 10% FCS 0.250 | 5% FCS 0.344 | 0% FCS 0.314 | No cells 0.085 |
| Mean - blank | 0.219 | 0.246 | 0.243 | 0.188 | 0.244 | 0.231 | 0.239 | 0.260 |
| | | | | | 10% FCS 0.165 | 5% FCS 0.259 | 0% FCS 0.229 | No cells 0.000 |
| St. Devtn. | 0.001 | 0.020 | 0.018 | 0.005 | 0.006 | 0.012 | 0.019 | 0.014 |
| | | | | | 10% FCS 0.011 | 5% FCS 0.011 | 0% FCS 0.035 | No cells 0.004 |

TABLE 6

Cell viability after 72 h contact time

| | Queuine 0.1 µg/ml | Queuine 1 µg/ml | Queuine 10 µg/ml | Queuine 100 µg/ml | Methanol 0.0006% | Methanol 0.006% | Methanol 0.06% | Methanol 0.6% |
|---|---|---|---|---|---|---|---|---|
| Mean OD values | 0.341 | 0.362 | 0.395 | 0.272 | 0.386 | 0.400 | 0.362 | 0.376 |
| | | | | | 10% FCS 0.259 | 5% FCS 0.429 | 0% FCS 0.466 | No cells 0.118 |
| Mean - blank | 0.223 | 0.244 | 0.277 | 0.154 | 0.268 | 0.282 | 0.244 | 0.259 |
| | | | | | 10% FCS 0.141 | 5% FCS 0.311 | 0% FCS 0.348 | No cells 0.000 |
| St. Devtn. | 0.035 | 0.024 | 0.010 | 0.010 | 0.017 | 0.026 | 0.011 | 0.028 |
| | | | | | 10% FCS 0.008 | 5% FCS 0.020 | 0% FCS 0.015 | No cells 0.001 |

Interpretation of Results

The negative and positive controls were in conformity and allowed validation of the experiment. Indeed, for the MTT assay, the 2.5% FCS control always scored higher than the 10% FCS control at 24 h.

The 2.5% FCS control was equivalent to the 10% FCS control at 48 h and lower than the latter at 72 h.

With regard to the carrier control alone (methanol range 0.6% to 0.0006%), this one exhibited a slight cytotoxic effect but with no dose effect and remained minimal. Therefore, its presence does not hinder cell physiology and will not hinder the remainder of the experiments even at its highest concentration. In addition, methanol is known to promote cell proliferation over the first few days.

With regard to the queuine molecule:

At 48 h, the concentration of 100 µg/ml exhibited a cytotoxic effect. The ODs obtained were similar to those of the negative control (0% FCS).

The other assayed concentrations below 100 µg/ml did not display any cytotoxic effect.

Cell Proliferation

TABLE 7

Cell viability after 24 h contact time

| | Queuine 0.3 µg/ml | Queuine 1 µg/ml | Queuine 3 µg/ml | Queuine 10 µg/ml | Queuine 30 µg/ml | Methanol 0.0018% | Methanol 0.006% | Methanol 0.018% | Methanol 0.06% | Methanol 0.18% |
|---|---|---|---|---|---|---|---|---|---|---|
| Mean ODs | 1.312 | 1.328 | 1.522 | 1.625 | 1.634 | 1.609 | 1.554 | 1.489 | 1.446 | 1.475 |
| | | | | | | | 0% FCS 0.158 | 2.5% FCS 1.355 | 10% FCS 1.939 | No cells 0.131 |
| Mean - blank | 1.181 | 1.197 | .391 | 1.494 | 1.502 | 1.477 | 1.423 | 1.357 | 1.314 | 1.344 |
| | | | | | | | 0% FCS 0.027 | 2.5% FCS 1.223 | 10% FCS 1.808 | No cells 0.000 |
| SD | 0.182 | 0.091 | 0.145 | 0.125 | 0.082 | 0.190 | 0.248 | 0.095 | 0.125 | 0.138 |
| | | | | | | | 0% FCS 0.003 | 2.5% FCS 0.042 | 10% FCS 0.126 | No cells 0.027 |

At 48 h and 72 h the incubation time in the presence of the substrate was deliberately shortened so that the OD values were not beyond the saturation threshold of the spectrophotometer.

After 5 h incubation at 37° C., the inserts were removed and the wells washed twice in PBS 1× to eliminate every non-adhering cell.

TABLE 8

Cell viability after 48 h contact time

|  | Queuine 0.3 µg/ml | Queuine 1 µg/ml | Queuine 3 µg/ml | Queuine 10 µg/ml | Queuine 30 µg/ml | Methanol 0.0018% | Methanol 0.006% | Methanol 0.018% | Methanol 0.06% | Methanol 0.18% |
|---|---|---|---|---|---|---|---|---|---|---|
| Mean ODs | 0.800 | 0.926 | 0.915 | 1.066 | 1.149 | 0.957 | 1.026 | 1.067 | 1.244 | 1.189 |
|  |  |  |  |  |  |  | 0% FCS 0.107 | 2.5% FCS 0.937 | 10% FCS 1.517 | No cells 0.123 |
| Mean - blank | 0.677 | 0.803 | 0.793 | 0.943 | 1.026 | 0.834 | 0.903 | 0.944 | 1.122 | 1.066 |
|  |  |  |  |  |  |  | 0% FCS −0.016 | 2.5% FCS 0.815 | 10% FCS 1.394 | No cells 0.000 |
| St. Devtn. | 0.068 | 0.126 | 0.129 | 0.050 | 0.143 | 0.083 | 0.108 | 0.113 | 0.068 | 0.016 |
|  |  |  |  |  |  |  | 0% FCS 0.003 | 2.5% FCS 0.074 | 10% FCS 0.167 | No cells 0.005 |

TABLE 9

Cell viability after 72 h contact time

|  | Queuine 0.3 µg/ml | Queuine 1 µg/ml | Queuine 3 µg/ml | Queuine 10 µg/ml | Queuine 30 µg/ml | Methanol 0.0018% | Methanol 0.006% | Methanol 0.018% | Methanol 0.06% | Methanol 0.18% |
|---|---|---|---|---|---|---|---|---|---|---|
| Mean ODs | 0.586 | 0.548 | 0.681 | 0.708 | 0.958 | 0.550 | 0.544 | 0.616 | 0.588 | 0.696 |
|  |  |  |  |  |  |  | 0% FCS 0.133 | 2.5% FCS 0.499 | 10% FCS 1.159 | No cells 0.170 |
| Mean - blank | 0.416 | 0.378 | 0.511 | 0.538 | 0.787 | 0.380 | 0.374 | 0.446 | 0.418 | 0.525 |
|  |  |  |  |  |  |  | 0% FCS −0.037 | 2.5% FCS 0.328 | 10% FCS 0.989 | No cells 0.000 |
| St. Devtn. | 0.033 | 0.108 | 0.009 | 0.041 | 0.061 | 0.061 | 0.075 | 0.070 | 0.082 | 0.019 |
|  |  |  |  |  |  |  | 0% FCS 0.009 | 2.5% FCS 0.059 | 10% FCS 0.062 | No cells 0.002 |

The protocol used was based on incubation without change of medium which leads to exhaustion of growth factor in the medium, particularly pronounced with the FCS chosen for the experiment (intended to ensure that it does not contain queuine, which would interfere with the experiment). As a result the OD per unit volume is lower compared with the shortest times.

Interpretation of Results

The negative and positive controls were in conformity and allowed validation of this experiment.

Indeed, for the BrdU assay, the 2.5% FCS control had less effect than the 10% FCS control irrespective of analysis time (24, 48 and 72 hours).

The "methanol" control (known to stimulate proliferation) displayed an effect:
close to that of queuine at 24 and 48 hours; and
lesser than that of queuine at 72 hours, on and after 3 µg/ml.

It can be concluded that:
queuine has no significant effect over short times (24 and 48 hours) compared with the carrier; and
a clear proliferative effect was evidenced at 72 hours at concentrations of 3 and 10 µg/ml, and particularly pronounced at a concentration of 30 µg/ml.

Cell Migration

The adult HDFs were seeded in the presence of previously sterilised culture inserts, to create calibrated acellular regions in a confluent cell mat. The cells tend to fill the gap created by migrating from the edges to close the gap.

Queuine was then added at 30, 10, 3 or 1 µg/ml in DMEM 2.5% FCS and an equivalent range of methanol was also prepared, two wells per condition.

Photos of the wells were taken at t=0 h.

The cells were cultured 24 h at 37° C., before being fixed in paraformaldehyde. Photos were taken at t=24 h.

3 controls were also evaluated, 2 wells/control:
serum-free DMEM;
serum-depleted medium (supplemented DMEM+2.5% FCS); and
complete medium (supplemented DMEM+10% FCS).

Figure 2:
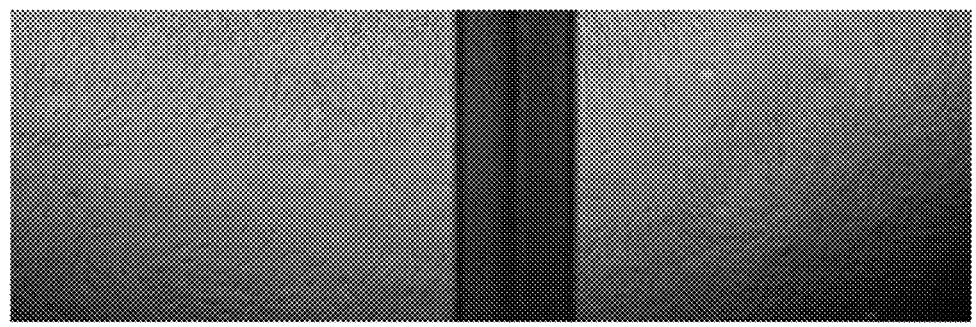

FIGS. 1 and 2 illustrate the effects of the DMEM 2.5% FCS control (corresponding to 0 µg/ml of molecule to be assayed—negative control) on the fibroblasts at 0 hours (FIGS. 1) and 24 hours FIG. 2), respectively.

Figure 3:
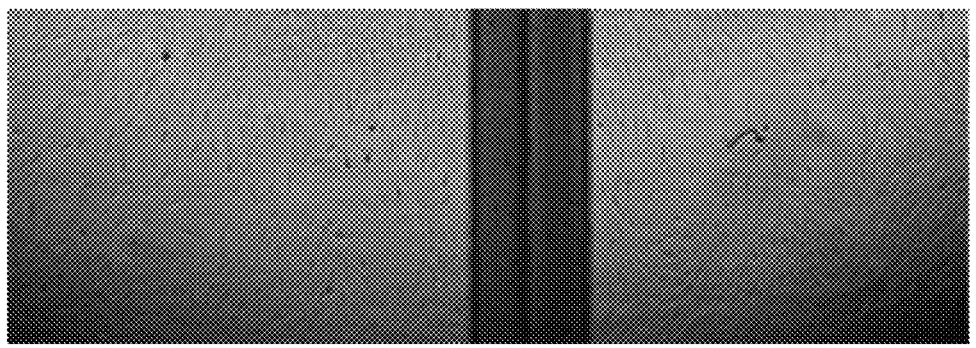

FIG. 3 illustrates the effects of the DMEM 10% FCS control (corresponding to the positive control) at 24 hours on the fibroblasts.

Figure 4:
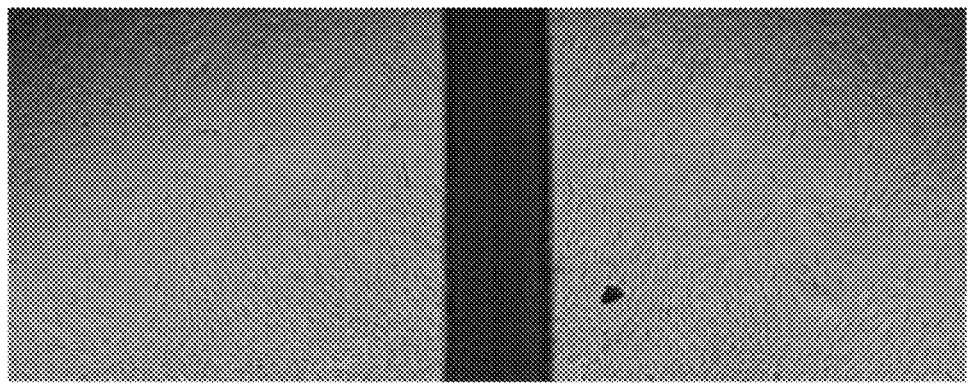
FIGS. 4 and 5 show cell migration in a fibroblast culture incubated with 10 µg/ml queuine in 2.5% FCS at 24 hours (FIG. 4) or 30 µg/ml queuine in 2.5% FCS at 24 hours (FIG. 5).
Figure 5:
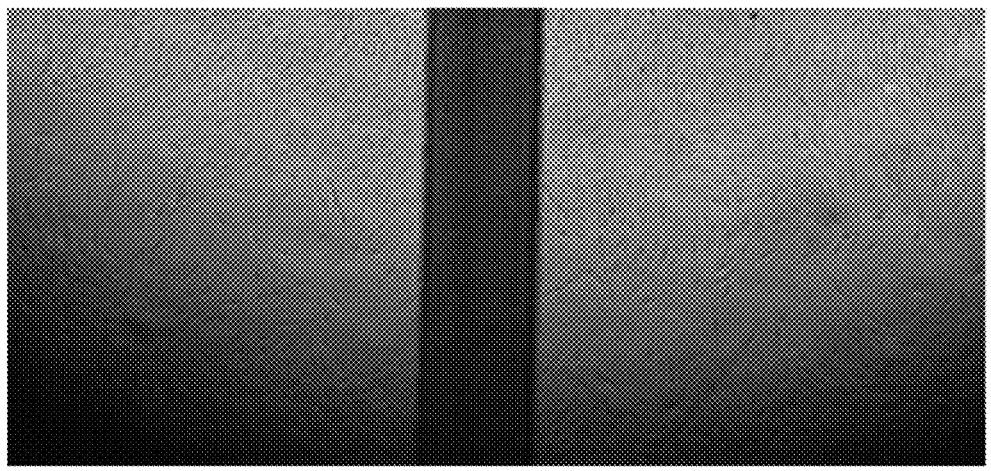

FIGS. 4 and 5 show the effects of queuine in 2.5% FCS at 24 hours on the fibroblasts, at concentrations of 10 µg/ml (FIG. 4) and 30 µg/ml (FIG. 5), respectively.

Figure 6:
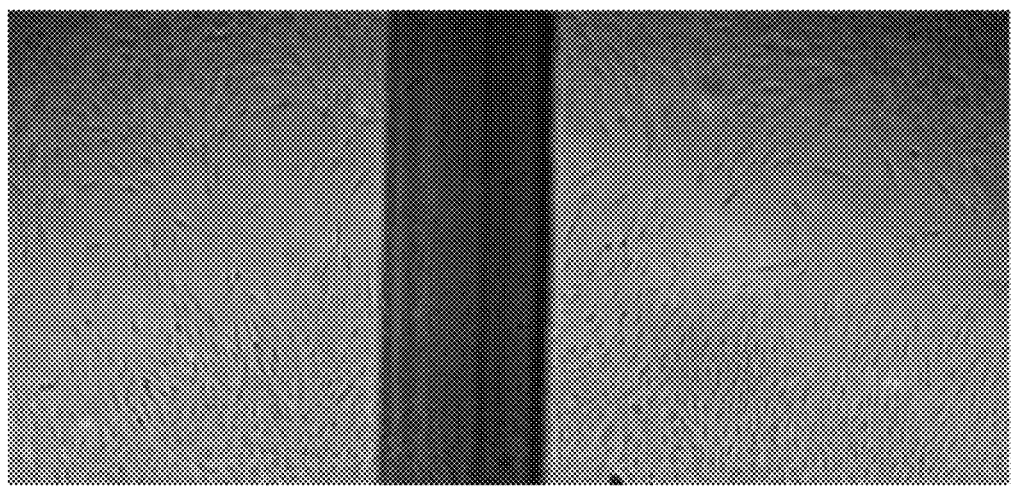
FIGS. 6 and 7 show cell migration in a fibroblast culture incubated with 10 µg/ml methanol in 2.5% FCS at 24 hours (FIG. 6) or 30 µg/ml methanol in 2.5% FCS at 24 hours (FIG. 7).
Figure 7:
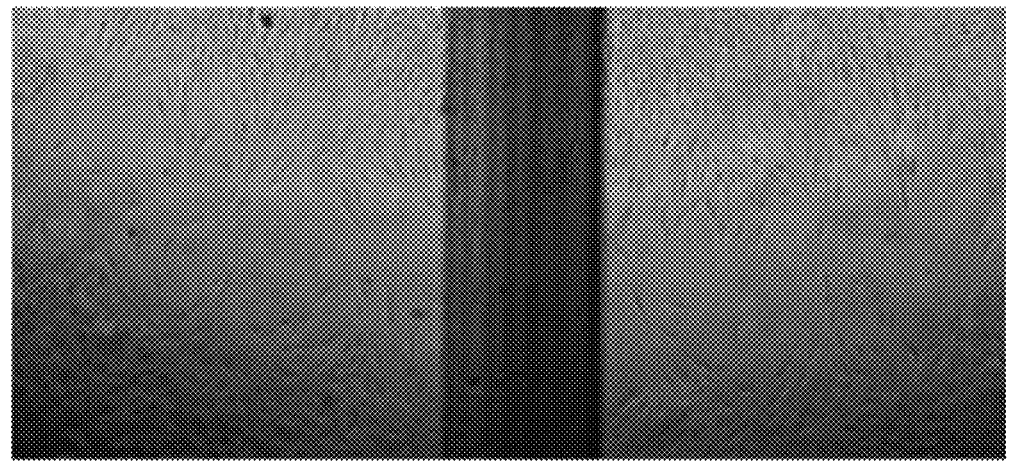

FIGS. 6 and 7 show the effects of methanol in DMEM 2.5% FCS at 24 hours on the fibroblasts, at concentrations of 10 µg/ml (FIG. 6) and 30 µg/ml (FIG. 7), respectively.

The black line which can be seen in all the Figures corresponds to marking applied to the back of the dishes to identify the regions to be photographed at 0 h and 24 h.

The photos were compared with each other to assess the difference in cell migration into the gap between the different assayed conditions.

It can be observed that compared with the 0 h condition, the cells in 2.5% FCS as in 10% FCS start to colonise the gap after 24 h. The cells turn in the direction of the opposite edge to migrate in this direction, whereas at the visible confluent cell mat the cytoplasmic extensions of the fibroblasts do not have any determined orientation. In addition it can be observed in these images that more cells in 10% FCS have migrated into the gap, and it is noteworthy that the cells arriving from the two opposite edges meet in the centre of the gap.

Observation of the photos for 10 µg/ml and 30 µg/ml queuine shows better migration than in 2.5% FCS. More cells can be seen in the gap while maintaining the shuttle orientation at the migration front towards the opposite edge, visible in 2.5% FCS. Finally at 30 µg/ml the cells of the two edges meet in the centre of the gap as can be seen in the presence of 10% FCS.

The results show that:
- The 2.5% FCS and 10% FCS controls exhibit migration proportional to % FCS used.
- Queuine has an effect on migration of the fibroblasts as early as the concentration of 10 µg/ml, and this effect on migration of the fibroblasts is confirmed at the concentration of 30 µg/ml.
- Migration in the presence of queuine at 10 and 30 µg/ml is equivalent to that obtained with the positive 10% FCS control.
- Methanol shows a slight effect on migration but not as clear as the effect of queuine.

General Conclusions

Concentrations lower than 100 µg/ml of queuine do not exhibit any cytotoxic effect on adult HDFs. In addition, a proliferative effect is evidenced with queuine at concentrations of 3, 10 and 30 µg/ml after 72 hours' incubation. A major proliferative effect is observed with queuine at a concentration of 30 µg/ml at 72 hours. Queuine has an effect on the migration of adult HDFs at a concentration of 10 µg/ml. This effect is confirmed at the concentration of 30 µg/ml. The migration in the presence of queuine at 10 and 30 µg/ml is equivalent to that obtained with the positive 10% FCS control.

Examples of Compositions

Basic Cream 6 volumes of aloe vera gel (which can be replaced by plant or mineral infusions or distilled water), 2.5 volumes of shea butter and jojoba oil mixture (can be replaced by any other vegetable oil or butter) and 1.5 volumes of emulsifying wax are carefully mixed. All the ingredients are placed over a hot water bath to allow the wax to melt, then vigorously mixed and placed on ice for cooling. The active ingredients are added. Finally methylparaben is added to a final concentration of 0.19% for preserving purposes.

Numerous manufacturers place neutral basic cosmetic creams on the market (e.g., Neutra Base©) and any base of an existing major brand can be improved by the invention.

Queuine is added to this base at a concentration of 0.1 mg per 100 ml.

For "organic" preparations, 100 mg of tRNA extract are added to 100 ml of basic cream.

Preparation of RNA Extracts Containing Queuine

Bacterial growth for biological preparation of queuine-containing extracts

Numerous growth media are suitable, for example, the following for Bacillus subtilis.

ED Medium

The ED growth medium contains: 8 mM $K_2HPO_4$; 4.4 mM $KH_2PO_4$; 27 mM glucose; 0.3 mM $Na_3$-citrate; 15 mM L-glutamine; 33.5 mM ammonium ferric citrate; and 2 mM $MgSO_4$. The trace elements are added to this base from a 100-times concentrated stock solution for a final concentration of: 0.61 mM $MgCl_2$; 49.5 mM $CaCl_2$; 49.9 mM $FeCl_3$; 5.05 mM $MnCl_2$; 12.4 mM $ZnCl_2$; 2.52 mM $CuCl_2$; 2.5 mM $CoCl_2$; and 2.48 mM $Na_2MoO_4$.

The wild-type strain of Bacillus subtilis is pre-cultured in liquid ED medium at 37° C. under constant aeration. A fresh overnight culture is inoculated in 15 ml of ED medium at an optical density of 0.1 to 600 nm (OD600). The cells are cultured at 37° C. up to an OD600 of 1 and cooled in an equal volume of 60% methanol in 70 mM HEPES buffer, pH 7.5 at −80° C. All the following steps are conducted under cold conditions and the solutions intended for the preparation of RNA are treated with diethyl pyrocarbonate and sterilised. The cells are pelleted at 4° C., washed in water and re-suspended in 0.5 ml 10% glucose, 11 mM Tris-HCL (pH 7.5), and 10 mM EDTA. The suspensions are transferred to tubes containing 0.1 g of acid-washed glass beads (Sigma-Aldrich, G4649).

The tubes are placed in a CoolPrep adapter of a FastPrep-24® instrument (MP Biomedical) containing 50 g of dry ice. The cells are fractionated in three cycles using the following parameters: 6 metres per second for 45 s. After each cycle the suspensions are held on ice for 1 min. After centrifuging 2 min at 10,000 rpm, the supernatant is transferred to a new Eppendorf tube. Sodium acetate, pH 5.2, is added to a final concentration of 0.3 M and the total RNA is isolated under acid conditions. One volume of phenol acid/chloroform and isoamyl alcohol (125:24:1) at pH 4.5 (Amresco, AM9720) is added. Each sample is vortexed 10 s and incubated for 3 min over a hot water bath at 65° C. The phases are separated by centrifugation 5 min at 14,000 rpm, and the aqueous phase is re-extracted once following the same hot acid phenol procedure. The aqueous phase is transferred to a new tube and completed with one volume of cold acid phenol. After centrifuging 5 min at 14,000 rpm, the RNA is precipitated with 2.5 volumes of absolute ethanol for 1 h at −80° C. The RNA is centrifuged at 14,000 rpm for 15 min at 4° C. and washed with 70% ethanol. The RNA pellet is dissolved in 10 mM Tris, 1 mM EDTA, pH 7.5. It can then be used as a first source of bacterial extract enriched with queuine.

Enriching with Transfer RNA

The preparation of total RNA described previously is mixed with one volume of 4.5 M lithium chloride, pH 8, with sodium acetate, pH 5.2, to a final concentration of 0.01 mM. This RNA solution is incubated 2 hours at −80° C. After centrifuging at 14,000 rpm for 15 min at 4° C., the tRNA is found in the supernatant. To remove salt contamination, the tRNA is precipitated 1 h at −80° C. through the addition of 0.3 M sodium acetate, pH 5.2, and 2.5 volumes of absolute ethanol. The tRNA is then caused to sediment by centrifuging at 14,000 rpm for 15 min at 4° C. and washed with 70% ethanol. The tRNA pellet is dissolved in 10 mM Tris, 1 mM EDTA, pH 7.5. This preparation is a preparation of transfer RNA rich in queuine. This preparation can subsequently be used as an active ingredient to prepare the cosmetic composition of the present invention.

The invention claimed is:

1. A method of reducing the signs of aging of the skin and/or skin appendages comprising the administration of queuine, or of a precursor or derivative thereof to the skin and/or skin appendages of a subject wherein the administration of queuine, or a precursor or derivative thereof reduces lines and wrinkles and/or sagging of the skin and/or lack of elasticity and/or tonicity of the skin and/or thinning of the skin and/or sallow and/or parchment-like complexion and/or irregularities of skin texture and pigmentation irregularities.

2. The method according to claim 1, wherein the queuine or precursor or derivative thereof is selected from queuine, queuosine and epoxyqueuine.

3. The method according to claim 1, wherein the queuine, a precursor or derivative thereof is in the form of a bacterial extract or plant extract or sap, said extract or said sap being rich in or enriched with queuine, a precursor or derivative thereof.

4. The method according to claim 1, wherein the queuine, the precursor or derivative thereof is administered in an amount of 0.1 μg to 100 μg per ml or g.

5. The method according to claim 1, wherein the queuine, the precursor or derivative thereof is administered with co-factors or vitamins.

6. The method according to claim 1, wherein the queuine, the precursor or derivative thereof is in the form of a serum, lotion, cream, milk, water or oil gel, hydrogel, mask, stick, patch, oil, unguent, wax, foam, toner, care solution, balm, foundation, spray, eye shadow, slimming cream, lipstick, paste, ointment or shampoo or conditioner.

7. The method according to claim 1, wherein the queuine, the precursor or derivative thereof is formulated for topical application.

* * * * *